United States Patent
Foo

(10) Patent No.: US 7,797,031 B1
(45) Date of Patent: Sep. 14, 2010

(54) METHOD AND APPARATUS FOR BREATH-HELD MR DATA ACQUISITION USING INTERLEAVED ACQUISITION

(75) Inventor: Thomas K. F. Foo, Potomac, MD (US)

(73) Assignee: General Electric Company, Schenectady, NY (US)

( * ) Notice: Subject to any disclaimer, the term of this patent is extended or adjusted under 35 U.S.C. 154(b) by 2097 days.

(21) Appl. No.: 10/249,914

(22) Filed: May 16, 2003

Related U.S. Application Data

(60) Provisional application No. 60/319,254, filed on May 17, 2002.

(51) Int. Cl.
*A61B 5/05* (2006.01)
(52) U.S. Cl. .................. 600/410; 600/413; 600/416
(58) Field of Classification Search .............. 600/410, 600/411, 413; 324/307, 309
See application file for complete search history.

(56) References Cited

U.S. PATENT DOCUMENTS

| | | | | |
|---|---|---|---|---|
| 5,377,680 | A * | 1/1995 | Bernstein et al. | 600/413 |
| 5,830,143 | A * | 11/1998 | Mistretta et al. | 600/420 |
| 6,147,493 | A * | 11/2000 | Miyoshi | 324/312 |
| 6,198,283 | B1 * | 3/2001 | Foo et al. | 324/309 |
| 6,201,985 | B1 * | 3/2001 | Polzin et al. | 600/411 |
| 6,400,151 | B1 * | 6/2002 | Haase et al. | 324/309 |
| 6,611,701 | B2 * | 8/2003 | Foo | 600/413 |
| 6,781,375 | B2 * | 8/2004 | Miyazaki et al. | 324/314 |

OTHER PUBLICATIONS

Wang, Yi et al. Breath-Hold Three-dimensional Contrast-enhanced Coronary MR Angiography: Motion-matched k-Space Sampling for Reducing Cardiac Motion Effects. Radiology 2000; 215:600-607.*
Lima, J. et al., Regional Heterogeneity of Human Myocardial Infarcts Demonstrated by Contrast-Enhanced MRI, Circulation, 1995, vol. 92, pp. 1117-1125.
Wu, K. et al., Quantification and Time Course of Microvascular Obstruction by Contrast-Enhanced Echocardiography and Magnetic Resonance Imaging Following Acute Myocardial Infatction and Reperfusion, JACC, 1998, vol. 32, pp. 1756-1764.

(Continued)

*Primary Examiner*—Brian Casler
*Assistant Examiner*—Nasir Shahrestani
(74) *Attorney, Agent, or Firm*—Ziolkowski Patent Solutions Group, SC

(57) ABSTRACT

A method and apparatus are presented for quickly acquiring MR cardiac images in a time equivalent to a single breath-hold. MR data acquisition is segmented across multiple cardiac cycles. MR data acquisition is interleaved from each phase of a first cardiac cycle with MR data from each phase of a subsequent cardiac cycle. Preferably, low spatial frequency data are interleaved between multiple cardiac cycles, and the subsequent cardiac cycle acquisition includes sequential acquisition of high spatial frequency data at the tail end of the acquisition window. An MR image can then be reconstructed with data acquired from each of the acquisitions that reduce ghosting and artifacts. MR images are reconstructed using this interleaved variable temporal k-space sampling technique to produce volume images of the heart within a single breath-hold. Images can be acquired throughout the cardiac cycle to measure ventricular volumes and ejection fractions. Single phase volume acquisitions can also be performed to assess myocardial infarction.

31 Claims, 4 Drawing Sheets

OTHER PUBLICATIONS

Wu, K. et al., Prognostic Significance of Microvascular Obstruction by Magnetic Resonance Imaging in Patients With Acute Myocardial Infarction, Circulation, 1998, vol. 97, pp. 765-772.

Kim, R. et al., Relationship of MRI Delayed Contrast Enhancement to Irreversible Injury, Infarct Age, and Contractile Function, Circulation, 1999, vol. 100, pp. 1992-2002.

Simonetti, O. et al., An Improved MR Imaging Technique for the Visualization of Myocardial Infarction, Radiology, 2001, vol. 218, pp. 215-223.

Kim, R. et al., The Use of Contrast-Enhanced Magnetic Resonance Imaging to Identify Reversible Myocardial Dysfunction, The New England Journal of Medicine, 2000, vol. 343, pp. 1445-1453.

Doyle, M. et al., Block Regional Interpolation Scheme for k-Space (BRISK): A Rapid Cardiac Imaging Technique, Magnetic Resonance in Medicine, 1995, vol. 33, pp. 163-170.

Doyle, M. et al., Rapid Cardiac Imaging with Turbo BRISK, Magnetic Resonance in Medicine, 1997, vol. 37. pp. 410-417.

Rochitte, C. et al., Magnitude and Time Course of Microvascular Obstruction and Tissue Injury After Acute Myocardial Infarction, Circulation, 1998, vol. 98, pp. 1006-1014.

Wolff, S. et al., Assessing Contrast on MR Images, Radiology, 1997, vol. 202, pp. 25-29.

Ehman, R. at al., Adaptive Technique for High-Definition MR Imaging of Moving Structures, Radiology, 1989, vol. 173, pp. 255-263.

Saranathan, M. et al., Fast Three-Dimensional Free Breathing Imaging of Myocardial Infarction, Proc. Intl. Soc. Mag. Reson. Med., 2002, p. 10.

Sodickson, D. et al., Simultaneous Acquisition of Spatial Harmonics (SMASH): Fast Imaging with Radiofrequency Coil Arrays, Magnetic Resonance in Medicine, 1997, vol. 38, pp. 591-603.

Pruessmann, K. et al., SENSE: Sensitivity Encoding for Fast MRI, Magnetic Resonance in Medicine, 1999, vol. 42, pp. 952-962.

Sodickson, D. et al., Tailored SMASH Image Reconstructions for Robust In Vivo Parallel MR Imaging, Magnetic Resonance in Medicine, 2000, vol. 44, pp. 243-251.

Foo, T. et al., Breath-held 3D Imaging of Delayed Hyper-enhancement for Assessment of Myocardial Viability using Variable Sampling in Time (VAST), International Society for Magnetic Resonance in Medicine, 2002.

* cited by examiner

METHOD AND APPARATUS FOR BREATH-HELD MR DATA ACQUISITION USING INTERLEAVED ACQUISITION

CROSS REFERENCE TO RELATED APPLICATIONS

The present application claims the benefit of U.S. Ser. No. 60/319,254 filed on May 17, 2002.

BACKGROUND OF INVENTION

The present invention relates generally to magnetic resonance imaging (MRI), and more particularly, to a method and apparatus for cardiac MR imaging using an interleaved variable sampling-in-time scheme for data acquisition.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$ may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

In imaging the heart, one has to contend with both respiratory motion and cardiac motion. The former being best controlled using a breath-held technique or some manner of respiratory compensation. Single-shot magnetic resonance imaging using Echo Planar Imaging (EPI) techniques are able to acquire an image in 50-100 msec, thereby eliminating cardiac motion artifacts, but result in low spatial resolution and image signal-to-noise ratio. Moreover, it is well known in the art that single-shot EPI acquisitions (including single shot spiral acquisitions) suffer from off-resonance effects which is manifested by either spatial distortion (with rectilinear readout) or spatial blurring (with spiral acquisitions).

Spatial resolution and image signal-to-noise ratio (S/N) is restored by segmenting the acquisition over several cardiac cycles. In order to minimize the image blurring that results from cardiac motion over several cardiac cycles, the segmented acquisition approach gates data acquisition such that data for the desired image is acquired over a small temporal window within each cardiac cycle and gated such that the acquisition occurs at the same phase of the cardiac cycle over subsequent acquisitions. The segmentation of data acquisition over several cardiac cycles is often referred to as a segmented k-space acquisition.

Such acquisition techniques yield images with high image signal-to-noise ratio and high spatial resolution. By keeping the data acquisition window within each cardiac cycle short, cardiac motion blurring over this temporal window is minimized. However, a smaller acquisition window implies greater segmentation where all necessary data required to reconstruct an image is spread out over a larger number of cardiac cycles and increases the breath-hold period (scan time). With two-dimensional image acquisition using gated segmented k-space techniques, acquisition windows of between 50-100 msec have been used for scan times of between 12-20 seconds.

Obviously, with three-dimensional imaging, the amount of data is substantially increased due to the need to spatially encode for the third slice direction. Hence, for images at the same in-plane spatial resolution as in a two-dimensional acquisition, the total scan time is increased by a factor equal to the number of slice partitions in the three-dimensional volume. As a result, using the same acquisition parameters as the two-dimensional acquisition renders the scan time of a three-dimensional acquisition to exceed a single breath-hold time for a typical patient suffering from cardio-vascular disease.

In current three-dimensional cardiac imaging, due to the longer scan times, data acquisition is either respiratory-gated or breath-held using segmented echo planar imaging (EPI). If respiratory-gated, 3D CINE images are acquired over several minutes, and the quality of the data acquisition is dependent on the patient maintaining a relatively stable respiration pattern over a period of 6-10 minutes. Images acquired using such breath-held 3D acquisitions are often characterized by low spatial resolution with only a single phase of the cardiac cycle acquired. The acquisition period has been reported to be between 20 and 40 seconds. Volumetric imaging is accomplished by acquiring data over several different breath-hold periods and combining the data acquisitions. However, after reconstructing images with data acquired over different breath-hold periods, temporal and spatial discrepancies and inaccuracies can occur, resulting in images that are not well defined and/or blurred. Moreover, in order to attain these shorter scan times, the acquisition window in the current 3D acquisitions are often long. Thus, the need to accommodate a shorter breath-hold period leads to increased spatial blurring from cardiac motion as a direct consequence of a larger data acquisition window within each cardiac cycle.

In addition, respiratory-gated techniques using navigator echoes for monitoring the respiratory motion do not lend themselves to a multi-phase or CINE acquisition as a separate pulse sequence section must also be played out within each cardiac interval to interrogate the displacement of the diaphragm. Furthermore, the acquisition of data for the different cardiac phases may not necessarily be at the same respiratory phase, leading to mixed image quality. This is so because some phase images closer to the time when the navigator echo segment was executed have better image quality than that more distant in time.

Such conventional methods for assessment of myocardial viability, involves the identification of regions of delayed hyper-enhancement following administration of a contrast bolus using an inversion recovery segmented k-space fast gradient recalled echo (FGRE) pulse sequence. This technique requires multiple 2D sections, each of which is acquired in a separate breath-hold. In order to cover the entire heart in a short axis view, typically, between 8-10 sections are required. With each section acquired in a breath-hold of generally 12-20 seconds, total scan time is between 6-9 minutes. The additional time allows the patient to recover between breath-holds.

Repeated breath-holding, however, often results in rapid patient fatigue. Moreover, the length of time between the acquisition of the first and last sections can also lead to varying degrees of normal myocardial suppression and hyper-enhancement of infracted tissue in the resulting images. Repeated breath-holding may also lead to increased inconsistency of the breath-hold position. As a result, improper registration of the individual 2D sections may occur and introduce error in the measurement of the infarct size or volume.

One imaging technique that is directed to solving the aforementioned concerns utilizes a near-single breath-hold 3D cardiac data acquisition using variable sampling-in-time (VAST). In the proposed method, low spatial frequency data is sampled with a smaller temporal window (higher temporal resolution) than high spatial frequency data. Notwithstanding the advantages achieved by this method, transitions in k-space can adversely affect image quality. That is, this technique can result in a sharp, distinct discontinuity between the high spatial frequency views and the low spatial frequency views that may generate ghosting and/or artifacts in the resulting image.

It would therefore be advantageous to implement a technique for single breath-hold 3D imaging that eliminates such sharp transition and therefore provides images without the ghost artifacts associated with spatial frequency transition/discontinuity.

SUMMARY OF INVENTION

The present invention relates to a technique for acquiring cardiac MR images in a time at least equivalent to a typical breath-hold using an interleaved variable temporal k-space sampling technique that solves the aforementioned problems. This fast, single breath-hold 3D acquisition can not only be used in a multi-phase acquisition for the diagnosis of cardiac wall motion abnormalities, evaluation of ventricular end-diastolic and end-systolic volumes, but also in a single phase mode with magnetization preparation (such as an inversion recovery rf pulse) for the evaluation of myocardial infarction or in coronary artery angiography.

While the present invention can be implemented in 2D or 3D acquisitions, the invention will primarily be described with reference to 3D acquisitions since one skilled in the art will readily understand how to implement the invention in a 2D acquisition, wherein the acquisition becomes a fast 2D acquisition technique that is able to acquire images every 2-3 heart beats in real-time An acquisition technique is disclosed that employs variable temporal sampling of 3D k-space to produce volume images of the heart within a reasonable breath-hold period. By performing an ECG-gated 3D single phase or multi-phase acquisition of the heart using fast gradient-recalled echo (FGRE) or steady-state free-precession (SSFP-FIESTA) pulse sequences, volumetric images can be generated during a time equivalent to a reasonable single breath-hold with minimal temporal and spatial discrepancies or inaccuracies as compared to images acquired over several different breath-hold periods.

An interleaved acquisition order is proposed that effectively moves the center of k-space closer to the start of the data acquisition segment and eliminates any abrupt transitions or discontinuities in k-space. In order to eliminate any abrupt transitions, an interleaved view acquisition order is implemented over multiple cardiac cycles. At least two heartbeats/cardiac cycles are required for each partition encoding view of the 3D volume. Low spatial frequency data is interleaved between the two cardiac cycles in which the first (temporal) acquisition window is smaller than a second acquisition window. The second acquisition window is larger to accommodate the acquisition of sequential high spatial frequency data at a tail end of the second acquisition window. By utilizing an interleaved and sequential view acquisition order, ghosting in the reconstructed image may be reduced.

In accordance with one aspect of the invention, a method of acquiring MR data includes segmenting data acquisition into a number of segments for a given slice acquisition and acquiring low spatial frequency MR data in one segment within a first acquisition window. The method also includes acquiring low and high spatial frequency MR data in another segment within a second acquisition window that is larger than the first acquisition window. Preferably, the acquisition of MR data in the low spatial frequency is performed relatively more often as compared to the acquisition of MR data in the high spatial frequency. This hybrid interleave-sequential acquisition scheme permits a smaller acquisition window during the acquisition of the first set of low spatial frequency data. At least a portion of the MR data is therefore acquired using an interleaved acquisition order to reduce transitional artifacts resulting from the separate acquisition of data from the low and high spatial frequency partitions. An MR image can then be reconstructed with the MR data acquired having reduced temporal and spatial inaccuracies to minimize cardiac motion blurring and/or artifacts.

According to another aspect of the present invention, a computer program is provided to control a medical imaging scanner. The computer program includes instructions to control a computer to segment data acquisition over at least two cardiac cycles and acquire a first set of MR data in a first acquisition window over a first cardiac cycle. The computer is further programmed to acquire a second set of MR data in a second acquisition window over a second cardiac cycle, wherein the second acquisition window is larger than the first acquisition window. The computer program further controls the computer to interleave the first set of MR data with at least a portion of the second set of MR data and reconstruct an MR image with the MR data acquired from each of the first and second sets of MR data. The computer is also programmed to begin MR data acquisition close to a center of k-space and progress outwardly to a periphery of k-space. This is done by first interleaving MR data acquisitions between two acquisition windows, and then sequentially acquiring remaining MR data in a second acquisition window of the two acquisition windows.

In accordance with yet another aspect of the present invention, a method of MR image acquisition is disclosed that includes segmenting MR data acquisition across multiple cardiac cycles and interleaving acquisition of MR data from each phase of a first cardiac cycle with MR data from each phase of a subsequent cardiac cycle. The process also includes acquiring additional MR data sequentially during the subsequent cardiac cycle and reconstructing an MR image with MR data acquired from each of the acquisitions.

In accordance with a further aspect of the present invention, an MRI apparatus is disclosed to acquire cardiac images and near single breath-hold times. The MRI apparatus includes a magnetic resonance imaging system having a plurality of gradient coils positioned about a bore of a magnet to impress a polarizing magnetic field and an RF transceiver system and an RF switch controlled by a pulse module to transmit RF signals to an RF coil assembly to acquire MR images. The MRI apparatus further includes a computer program to segment MR data acquisition across more than one acquisition window. The proposed technique of segmenting unequal number of views minimizes k-space transition artifacts and provides better $T_1$ weighting by beginning a data acquisition closer to the center of k-space.

The invention can be used for efficient single 3D breath-hold evaluations of myocardial delayed enhancement (MDE). Additionally, the present technique is applicable to elliptical centric view acquisition orders where the first segment can be an interleaved acquisition order acquiring every other view in an elliptical centric trajectory through the $k_y k_z$ space for the central two N views and for every view in the sequential acquisition for the remaining k-space views along the elliptical centric trajectory. The technique results in images yielding better definition of infarctions and myocardial boundaries.

Various other features, objects and advantages of the present invention will be made apparent from the following detailed description and the drawings.

BRIEF DESCRIPTION OF DRAWINGS

The drawings illustrate one preferred embodiment presently contemplated for carrying out the invention.

In the drawings.

DETAILED DESCRIPTION

Figure 1:
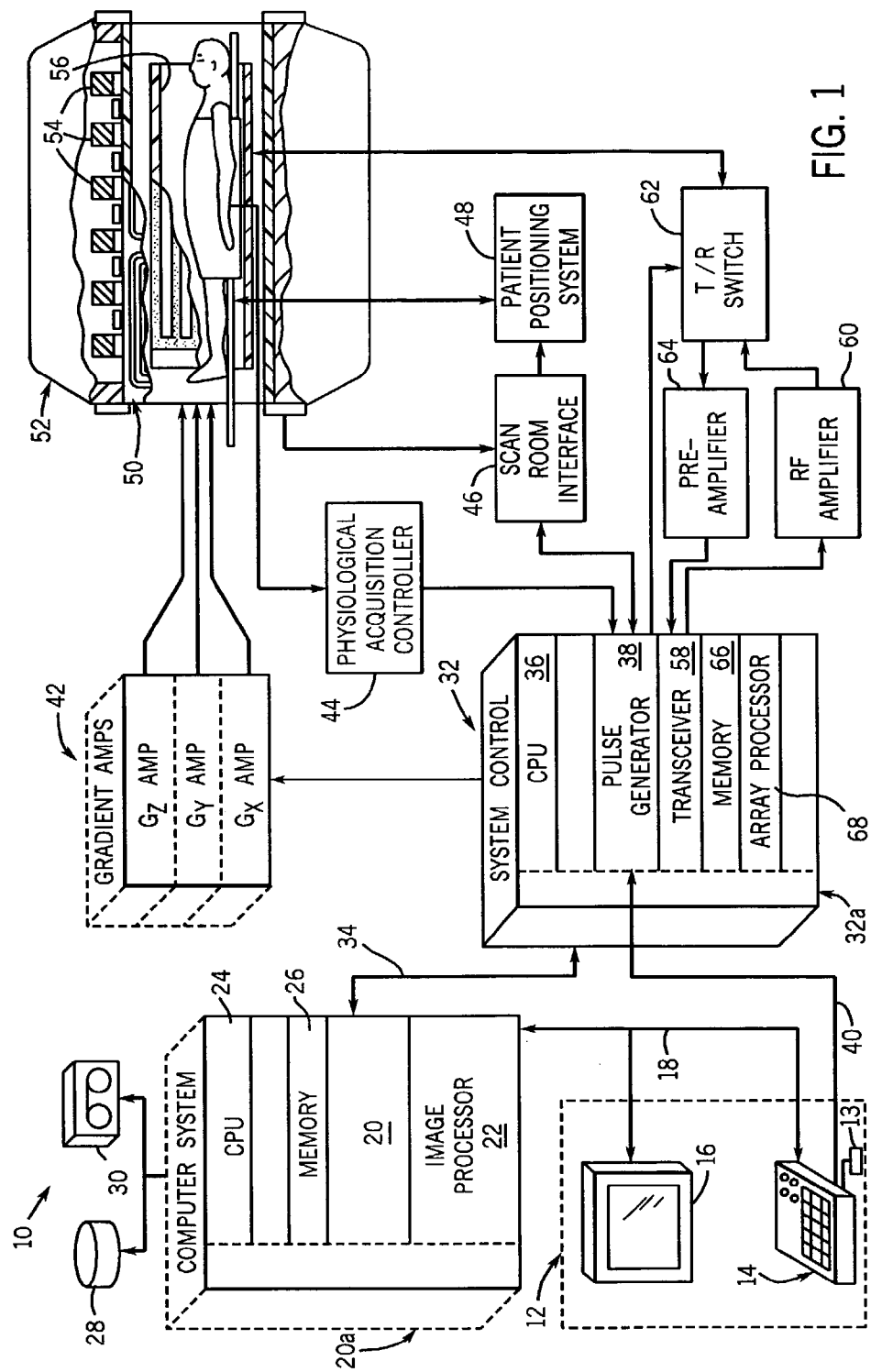
FIG. 1 is a schematic block diagram of an NMR imaging system for use with the present invention.

Referring to FIG. 1, the major components of a preferred MRI system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to a disk storage 28 and a tape drive 30 for storage of image data and programs, and it communicates with a separate system control 32 through a high speed serial link 34. The input device 13 can include a mouse, joystick, keyboard, track ball, touch screen, light wand, voice control, or similar device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator which indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 also receives patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in an assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 during the receive mode. The transmit/receive switch 62 also enables a separate RF coil (for example, a surface coil) to be used in either the transmit or receive mode.

The MR signals picked up by the RF coil 56 are digitized by the transceiver module 58 and transferred to a memory module 66 in the system control 32. When a scan is completed, an array of raw k-space data has been acquired in the memory module 66. As will be described in more detail below, this raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in the disk memory 28. In response to commands received from the operator console 12, this image data may be archived on the tape drive 30, or it may be further processed by the image processor 22 and conveyed to the operator console 12 and presented on the display 16.

The present invention includes a method and system suitable for use with the above-referenced NMR system, or any similar or equivalent system for obtaining MR images.

In order to minimize cardiac motion blurring, it is advantageous to maintain a short acquisition window within each cardiac cycle in gated-3D volume acquisitions. Additionally, the total scan time must be short to allow for a reasonable breath-hold period. For example, a typical 256×192 partial Fourier acquisition of 16 slice partitions would require a total scan time of approximately 112 heartbeats assuming that all 16 slices including views are acquired within each R-R cardiac interval. That is, for each cardiac interval, 16 separate data acquisitions occur within a small temporal window with each separate data acquisition at a different slice encoding ($k_z$) values with the same phase encoding value ($k_y$). During the next cardiac interval, the phase encoding value ($k_y$) is incremented and the data acquisition repeats for all the slice encoding ($k_z$) values. This continues until all necessary data are acquired. The present invention utilizes a variable interleaved temporal k-space sampling scheme in order to reduce this acquisition time to within approximately 24 heartbeats, which is a time period more amenable for a single breath-hold. The total scan time is reduced by acquiring low $k_y$ spatial frequency views in a smaller temporal acquisition window than high $k_y$ spatial frequency views. By being able to acquire the higher spatial frequency views in a larger temporal acquisition window, more k-space lines of data can be acquired, speeding up data acquisition. Spatial blurring and motion artifacts are minimized by acquiring the low spatial frequency views in a smaller acquisition window. This is in contrast to a more conventional segmentation where the high and low spatial frequency views are segmented in acquisition windows of equal temporal duration.

The present technique includes the use of a short acquisition window for the low $k_y$ spatial frequency views acquired in a first acquisition window and a longer subsequent acquisition window for both low and high $k_y$ spatial frequency views.

Figure 2:
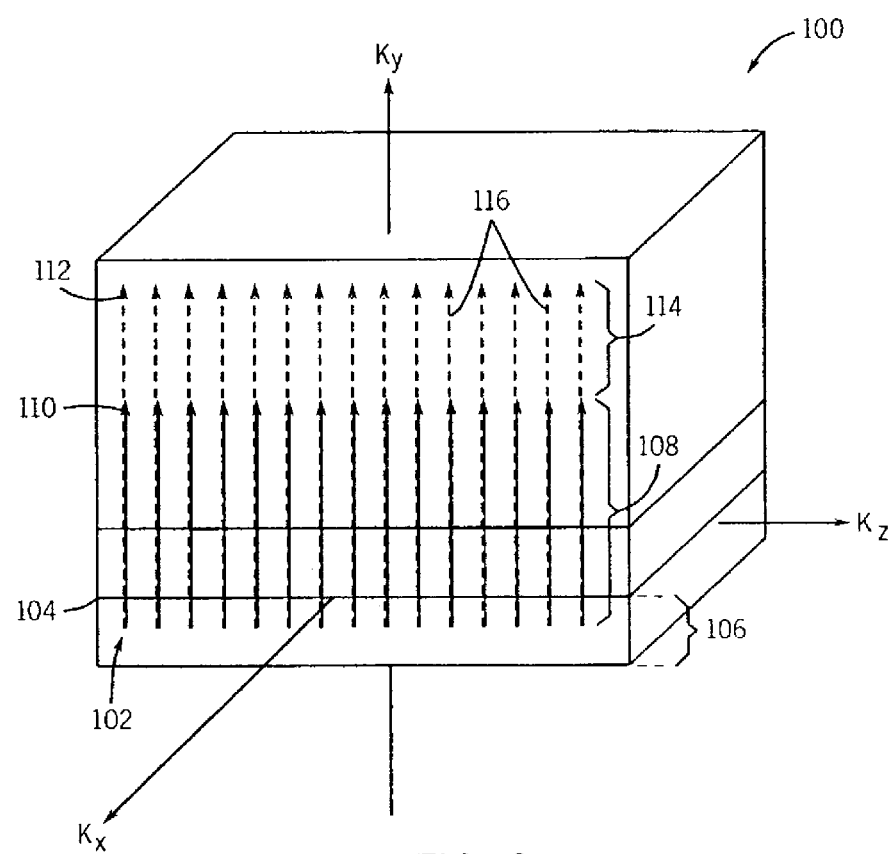
FIG. 2 shows a data acquisition and arrangement scheme in accordance with one embodiment of the present invention.

FIG. 2 is a three dimensional representation of a data acquisition and organization scheme in accordance with the present invention. An interleaved acquisition order 100 is shown that moves the start of data acquisition 102 closer to a center of k-space 104 in order to eliminate any abrupt transitions in k-space resulting from the junction of high spatial frequency data and low spatial frequency data, as will be described with reference to FIG. 4. As indicated in FIG. 2, the acquisition and organization of $k_y$ views is interleaved at 108. Although for representation sake the individual lines 110, 112 are shown offset slightly, it is understood that the interleaving acquisition actually results on a first acquisition 110 directly under a second acquisition 112. The lines for acquisitions 112 extend beyond acquisitions 110 and are grouped together at 114 to indicate a sequential acquisition of high spatial frequency MR data 116. As heretofore described, acquisition of the $k_y$ views begins at the over-scan region 106 and proceeds through the center of k-space 104. Thus, a number of $k_y$ views are played out before the center of k-space is sampled, but the sampling is close enough to the center of k-space to result in significant improvement. Typically, 16-20 $k_y$ views result from the over-scan region.

By moving the onset of data acquisition closer to the center of k-space, and interleaving the acquisition of the $k_y$ views, the aforementioned artifacts resulting from the transition between high spatial frequency and low spatial frequency views is significantly reduced. Specifically, using a fractional NEX acquisition in the $k_y$ direction, the MR data acquisition is partitioned into a low and a high spatial frequency partitions with the low spatial frequency partition having n views and the high spatial frequency partition having greater than n views. An interleaved acquisition would result in rhhnover/2 TR intervals prior to the reaching of the center of k-space. "Rhhnover" corresponds to the number of views played out prior to the sampling of the center of k-space. Moreover, 2n views would be acquired at approximately the same time in the cardiac cycle with remaining high spatial frequency views being acquired beyond the acquisition window of the low spatial frequency partition.

Figure 3:
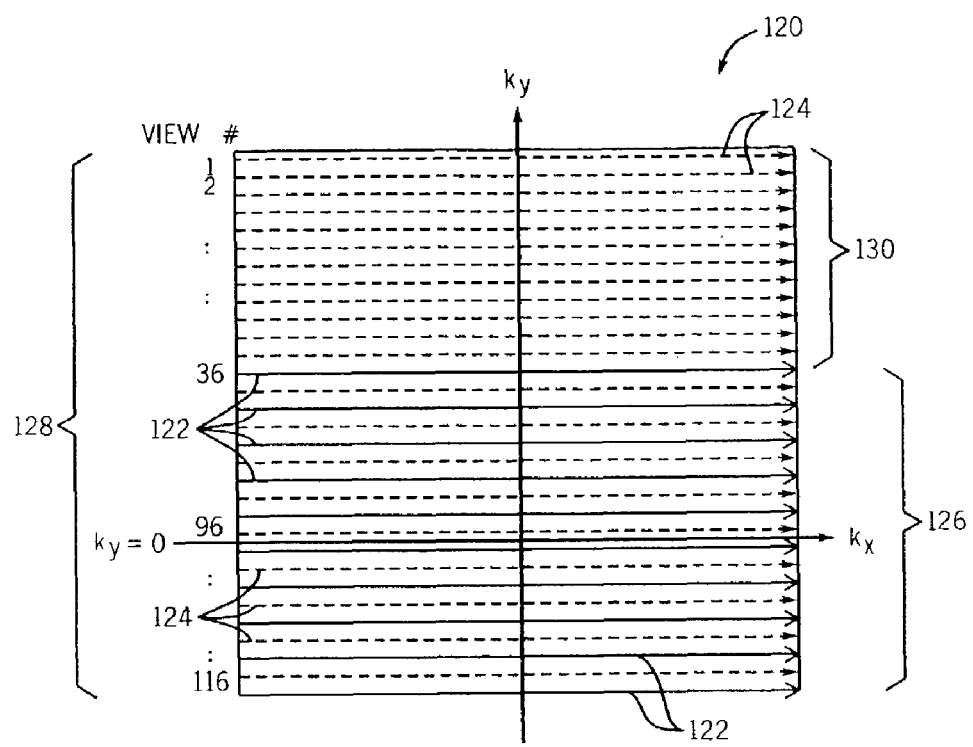
FIG. 3 shows an acquisition order used to acquire the data shown in FIG. 2 across two R-R intervals.

FIG. 3 shows an acquisition order for the segmentation acquisition of the present invention across two R-R intervals (cardiac cycles). In this example, 116 total views are acquired in a half-Fourier acquisition with view #96 representing the center of k-space and view #1 representing the highest spatial frequency encoded in the phase encoding ($k_y$) direction. The views indicated by solid lines 122 are acquired in a first R-R interval and the remaining views, represented by dashed lines 124, are acquired in a subsequent R-R interval for each partition encoding step. In a preferred embodiment, the subsequent R-R interval is the next cardiac cycle after the first cardiac cycle, although, it is contemplated that a cardiac cycle could be skipped, if so desired. As indicated, the acquisition, of a first set of MR data 122 is acquired in a first acquisition window 126 over the first cardiac cycle in the series. A second set of MR data represented by views 124 is acquired in a second acquisition window 128 over a second cardiac cycle. In this manner, the low spatial resolution views are interleaved between the two cardiac cycles within window 126, while the high spatial resolution views are acquired sequentially at 130, in the tail end of window 128.

Assuming that 2n rhnnover views are acquired in the low spatial frequency segment and the remaining views are acquired in subsequent segments, the central 4n rhnnover views are acquired in an interleaved acquisition order and the remaining views are sampled in a sequential order in the high spatial frequency segment. As such, a hybrid interleaved-sequential acquisition order is implemented that samples an unequal number of views in each segment. Dummy rf excitations may be used at the end of the high spatial frequency segment to provide a steady state that is similar to that of the second and subsequent segments. For example, if 32 views are acquired in the first segment and 52 views are acquired in the second segment, 20 dummy rf excitations may be used (at the end of the shorter acquisition window) to maintain a consistent dynamic equilibrium for all segments.

In accordance with this technique, segments of unequal number of views is acquired to minimize k-space transition artifacts and to provide better $T_1$ weighting by moving the start of the data acquisition closer to the center of k-space. As such, better weighting of central k-space views is provided. It should be noted that this technique is also applicable to elliptical centric view acquisition orders wherein the first segment may be an interleaved acquisition order acquiring every other view in an elliptical centric trajectory through $k_y k_z$ space for the central 2n views and a sequential order for the remaining k-space views along the elliptical centric trajectory.

Figure 4:
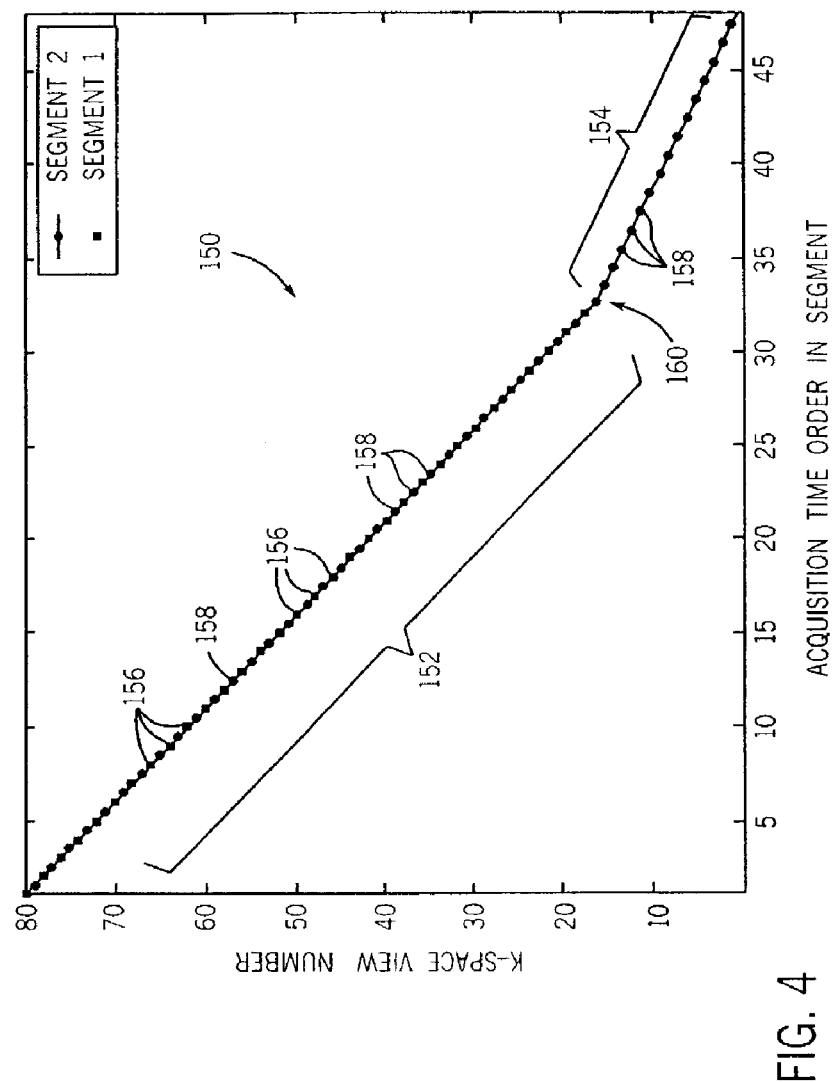
FIG. 4 is a graphical representation of acquisition time order versus k-space view number in accordance with the present invention.

The hybrid interleaved/sequential acquisition order of the present invention is graphically illustrated in FIG. 4. Acquisition order 150 is shown for two segments or R-R intervals and is oriented such that the "k-space view number" corresponds to the vertical axis and "acquisition time order in segment" corresponds to the horizontal axis. As shown, MR data is acquired in the low spatial frequency partition 152 in an interleaved fashion and the MR data in high spatial frequency partition 154 is acquired in a sequential order. The data acquired in the first segment 156 is represented with rectangular data points, and the data acquired in the second segment is represented with circular data points 158. The acquisition window for the second segment 158 is markedly larger than that of the first. Accordingly, one skilled in the art will readily appreciate that the number of views acquired in the first segment 156 is less than the number of views acquired in the second segment 158.

Still referring to FIG. 4, a first portion of the low spatial frequency partition 152 is acquired in the first segment 156 or first R-R interval, and the second or remaining portion of partition 152 is acquired in the second segment 158 or subsequent R-R interval. This "interleaved" acquisition of the low spatial frequency partition 152 improves image quality by moving the start of data acquisition closer to the center of k-space. Furthermore, this technique allows imaging outwardly toward the periphery of k-space thereby reducing ghosting artifacts as a result of the transition between high spatial frequency views and low spatial frequency views in the resulting MR image. In other words, acquisition during a first segment or cardiac cycle, a first portion of the low spatial frequency partition is acquired, and during a second segment, or subsequent cardiac cycle, the remaining portion of the low spatial frequency partition is acquired, as well as the high spatial frequency MR data. The MR data of the low spatial frequency partition is then acquired in an interleaved acquisition order, whereas the MR data of the high spatial frequency partition is acquired with a sequential acquisition order. FIG. 8 therefore shows a relatively smooth transition at 160 in the time order of the acquisitions that results in the reduction of artifacts and/or ghosts.

Implementation of the present hybrid interleaved/sequential technique with a 3D breath-hold gated acquisition using an NVE 256×160/0.5 NEX partial Fourier acquisition, whole heart coverage with a single volume acquisition can be achieved in just 24 heartbeats. Experimental studies were conducted using a 1.5T SIGNA CV/i cardiac MR scanner from GE Medical Systems, Waukesha, Wis., using high performance gradients (40 mT/m, 150 T/m/s) with fast, three dimensional gradient recalled echo (3DFGRE) pulse sequences modified to allow inversion-recovery prepared segmented ECG-gated acquisition. Images were acquired in mid-to-end systole. The acquisition window for the low k-space views was about 138 milliseconds while the acquisition window with the high k-space views was about 206 milliseconds, assuming a TR time of 3.3 4.3 milliseconds and 12 slice partitions. In this example, there were 32 views in each segment of the low spatial frequency data and 48 views of the high spatial frequency data.

The resulting images have better edge definition and fewer artifacts than in images not employing the hybrid interleaved-sequential acquisition order presented herein. The ability to rapidly acquire images from a 3D volume in a single breath-hold can thus be achieved, without the use of parallel imaging techniques. However, it is well understood that the present invention is readily applicable with parallel imaging, and hence, the overall scan time can be reduced by a factor of two or more. Alternatively, the reduction in scan time can be forsaken to improve temporal and spatial resolution. The present invention provides a technique that is especially applicable to the visualization of myocardial infarction. In addition to reducing transition artifacts and/or ghosts, increased infarct visualization and contrast-to-noise ratio was improved with whole heart coverage with a single volume acquisition achieved in 24 heartbeats. The examination time for a myocardial viability study can thus be reduced to a single breath-hold. Additionally, this fast acquisition scheme allows repeated acquisitions at different TI times for global $T_1$ measurements of the whole heart without correcting for changes in gadolinium contrast concentration as encountered with whole heart 2D scans. In addition, the 3D approach can be used in an end-inspiration breath-hold acquisition as there is no need to obtain multiple reproducible end-expiratory breath-hold positions, as in 2D studies. Not only is patient tolerance improved, but also fatigue is reduced.

Accordingly, the aforementioned technique is implemented in a computer program, and run on a computer system to control an imaging device, such as that described with reference to FIG. 1. The apparatus and method of the present invention is capable of obtaining images, each of a different phase of the cardiac cycle in a 3D volume in a single breath-hold with high image S/N. Another advantage of a 3D acquisition is the ability to reformat images of the heart and generate data that is ideal for a 3D rendering of the ventricular volume, which is particularly advantageous for more accurate volumetric and functional analysis of cardiac output.

The present invention has been described in terms of the preferred embodiment, and it is recognized that equivalents, alternatives, and modifications, aside from those expressly stated, are possible and within the scope of the appending claims.

The invention claimed is:

1. A method of acquiring MR data comprising the steps of:
    segmenting data acquisition into a number of segments for a given slice acquisition;
    selecting one segment to acquire an amount of MR data unequal to an amount of MR data to be acquired in another segment;
    acquiring low spatial frequency MR data in the one segment within a first acquisition window;
    acquiring low and high spatial frequency MR data in the another segment within a second acquisition window that is larger than the first acquisition window;
    interleaving the acquisition of the low spatial frequency MR data between the first and second acquisition windows; and
    reconstructing an MR image using the MR data of the first and second acquisition windows.

2. The method of claim 1 wherein the high spatial frequency MR data is acquired sequentially.

3. The method of claim 1 wherein the MR data is acquired over two R-R intervals per slice location or partition encoding view.

4. The method of claim 1 further comprising applying a pulse sequence having a magnetization preparation segment applied before image acquisition.

5. The method of claim 4 wherein the magnetization preparation segment is an inversion recovery RF pulse.

6. The method of claim 5 wherein MR data at a center of k-space is acquired after one of approximately eight RF excitation pulses and close to a start of data acquisition.

7. The method of claim 1 further comprising the step of acquiring MR data in the presence of cardiac motion and grouping the high spatial frequency MR data into a single acquisition window to reduce motion artifacts.

8. An MRI apparatus to rapidly acquire MR images comprising:
    a magnetic resonance imaging (MRI) system having a plurality of gradient coils positioned about a bore of a magnet to impress a polarizing magnetic field and an RF transceiver system and an RF switch controlled by a pulse module to transmit RF signals to an RF coil assembly to acquire MR images; and
    a computer programmed to:
        segment MR data acquisition across more than one acquisition window; and
        begin MR data acquisition for a given slice image close to a center of k-space and progress outwardly to a periphery of k-space by:
            first interleave low spatial frequency MR data acquisitions of a first acquisition window with low spatial frequency MR data acquisitions of a second acquisition window; and then,
            sequentially acquire remaining MR data in a second acquisition window of the two acquisition windows.

9. The MRI apparatus of claim 8 wherein the interleaved MR data comprises essentially all acquired low spatial frequency data and the sequentially acquired MR data is comprised essentially of high frequency data.

10. The MRI apparatus of claim 8 wherein the computer further combines each slice of MR data acquired in one acquisition window with each slice of corresponding MR data that is interleaved in a next acquisition window.

11. The MRI apparatus of claim 8 wherein a first acquisition window is smaller than the second acquisition window.

12. The apparatus of claim 8 wherein the computer is further programmed to reconstruct an MR image with MR data acquired from each acquisition window and each acquisition window corresponds to a respective R-R interval of a cardiac cycle.

13. A nontransitory computer readable storage medium having a computer program stored thereon to control a medical imaging scanner and representing instructions that when executed by a computer cause the computer to:
segment data acquisition over at least two cardiac cycles;
acquire a first set of MR data in a first acquisition window over a first cardiac cycle;
acquire a second set of MR data in a second acquisition window over a second cardiac cycle, wherein the second acquisition window is larger than the first acquisition window;
interleave the first set of MR data with a portion of the second set of MR data; and
reconstruct an MR image with the MR data acquired from each of the first and second sets of MR data.

14. The nontransitory computer readable storage medium of claim 13 wherein the instructions further cause the computer to acquire low spatial frequency MR data in each acquisition window and a majority of high spatial frequency MR data in the secondary acquisition window.

15. The nontransitory computer readable storage medium of claim 13 wherein 32 lines of data are acquired in the first acquisition window and 96 lines of data are acquired in the second acquisition window.

16. A method of MR image acquisition comprising:
segmenting MR data acquisition across multiple cardiac cycles;
partitioning MR data acquisition into at least low and high spatial frequency view partitions;
acquiring MR data during a first cardiac cycle for a shorter period of time than during a subsequent cardiac cycle;
interleaving acquisition of low spatial frequency MR data from each phase of the first cardiac cycle with low spatial frequency MR data from each phase of the subsequent cardiac cycle;
acquiring high spatial frequency MR data sequentially during the subsequent cardiac cycle after acquisition of low spatial frequency MR data during the subsequent cycle; and
reconstructing an MR image with MR data acquired from each of the acquisitions.

17. The method of claim 16 wherein reconstructing an MR image comprises reconstructing a volume image of a cardiac region of a patient during a single breath-hold.

18. The method of claim 17 wherein the volume image includes a cardiac image acquired at either one of diastole and systole.

19. The method of claim 16 further comprising the step of acquiring MR data from a proximate center of k-space to a periphery of k-space to minimize amplitude and phase transitions from the acquisition of MR data from the low and high spatial frequency view partitions.

20. The method of claim 16 further comprising applying a fat suppression magnetization preparation segment.

21. The method of claim 16 further comprising applying both a fat suppression and a recovery magnetization preparation segment.

22. The method of claim 21 wherein the recovery magnetization preparation segment is an inversion-recovery or a saturation recovery magnetization preparation segment.

23. The method of claim 16 further comprising acquiring MR data at a rate of 1 image every 2 to 3 cardiac intervals, and reconstructing a 2D image to provide real-time imaging capabilities with a patient in free-breathing.

24. The method of claim 20 further comprising acquiring data for coronary artery imaging.

25. A method of acquiring MR data comprising the steps of:
segmenting data acquisition into a number of segments for a given slice acquisition;
selecting one segment to acquire an amount of MR data unequal to an amount of MR data to be acquired in another segment;
acquiring low spatial frequency MR data in the one segment within a first acquisition window;
acquiring low and high spatial frequency MR data using the RF coil assembly in another segment within a second acquisition window that is larger than the first acquisition window;
reconstructing an MR image using the MR data of the first and second acquisition windows; and
wherein every other line of low spatial frequency MR data is acquired in alternating acquisition segments.

26. A method of acquiring MR data comprising the steps of:
segmenting data acquisition into a number of segments for a given slice acquisition;
selecting one segment to acquire an amount of MR data unequal to an amount of MR data to be acquired in another segment
acquiring low spatial frequency MR data in the one segment within a first acquisition window;
acquiring low and high spatial frequency MR data in another segment within a second acquisition window that is larger than the first acquisition window;
wherein the number of segments is equal to a number of R-R intervals that MR data is sought to be acquired; and
reconstructing an MR image using MR data acquired from each of the acquisition segments.

27. A method of acquiring MR data comprising:
segmenting data acquisition into a number of segments for a given slice acquisition;
selecting one segment to acquire an amount of MR data unequal to an amount of MR data to be acquired in another segment;
acquiring low spatial frequency MR data in the one segment within a first acquisition window;
acquiring low and high spatial frequency MR data in the another segment within a second acquisition window that is larger than the first acquisition window, wherein the low and high spatial frequency MR data is acquired over two R-R intervals per slice location or partition encoding view; and
reconstructing an MR image using the MR data of the first and second acquisition windows.

28. A method of acquiring MR data comprising:
segmenting data acquisition into a number of segments for a given slice acquisition;
selecting one segment to acquire an amount of MR data unequal to an amount of MR data to be acquired in another segment;
applying a pulse sequence having a magnetization preparation segment applied before image acquisition;
acquiring low spatial frequency MR data in the one segment within a first acquisition window after applying a magnetization preparation segment;
acquiring low and high spatial frequency MR data in the another segment within a second acquisition window that is larger than the first acquisition window after a second application of the magnetization preparation segment; and reconstructing an MR image using the MR data of the first and second acquisition windows.

29. A method of MR image acquisition comprising:

segmenting MR data acquisition across multiple cardiac cycles;

acquiring MR data during a first cardiac cycle for a shorter period of time than during a subsequent cardiac cycle;

interleaving acquisition of MR data from each phase of the first cardiac cycle with MR data from each phase of the subsequent cardiac cycle;

acquiring additional MR data sequentially during the subsequent cardiac cycle; and reconstructing an MR image with MR data acquired from each of the acquisitions during a single breath-hold, wherein the MR image is a volume image of a cardiac region.

30. A method of MR image acquisition comprising:

segmenting MR data acquisition across multiple cardiac cycles;

applying a fat suppression magnetization preparation segment;

acquiring MR data during a first cardiac cycle for a shorter period of time than during a subsequent cardiac cycle;

interleaving acquisition of MR data from each phase of the first cardiac cycle with MR data from each phase of the subsequent cardiac cycle;

acquiring additional MR data sequentially during the subsequent cardiac cycle; and reconstructing an MR image with MR data acquired from each of the acquisitions.

31. A method of MR image acquisition comprising:

segmenting MR data acquisition across multiple cardiac cycles;

acquiring MR data during a first cardiac cycle for a shorter period of time than during a subsequent cardiac cycle;

interleaving acquisition of MR data from each phase of the first cardiac cycle with MR data from each phase of the subsequent cardiac cycle;

acquiring additional MR data sequentially during the subsequent cardiac cycle, wherein the MR data and the additional MR data is acquired at a rate of 1 image every 2 to 3 intervals; and reconstructing an 2D MR image with MR data acquired from each of the acquisitions to provide real-time imaging capabilities with a patient in free-breathing.

* * * * *